(12) United States Patent
Thornton et al.

(10) Patent No.: US 10,752,962 B2
(45) Date of Patent: Aug. 25, 2020

(54) **DETECTION OF *NEISSERIA GONORRHOEAES***

(71) Applicant: Becton, Dickinson and Company, Franklin Lakes, NJ (US)

(72) Inventors: Keith Edward Thornton, Owings Mills, MD (US); Paul Madepogu, Baltimore, MD (US); Danielle Koffenberger, Intervale, NH (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/001,868

(22) Filed: Jun. 6, 2018

(65) Prior Publication Data
US 2019/0002961 A1    Jan. 3, 2019

Related U.S. Application Data

(62) Division of application No. 14/775,941, filed as application No. PCT/US2014/021949 on Mar. 7, 2014, now Pat. No. 9,994,916.

(60) Provisional application No. 61/798,757, filed on Mar. 15, 2013.

(51) Int. Cl.
*C12Q 1/689* (2018.01)
*C12Q 1/6883* (2018.01)

(52) U.S. Cl.
CPC ........... *C12Q 1/689* (2013.01); *C12Q 1/6883* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,988,617 A | 1/1991 | Landegren et al. |
| 5,130,238 A | 7/1992 | Malek et al. |
| 5,399,491 A | 3/1995 | Kacian et al. |
| 5,422,252 A | 6/1995 | Walker et al. |
| 5,427,930 A | 6/1995 | Birkenmeyer et al. |
| 5,455,166 A | 10/1995 | Walker |
| 5,849,478 A | 12/1998 | Cashman |
| 5,854,033 A | 12/1998 | Lizardi |
| 5,866,366 A | 2/1999 | Kallender |
| 6,090,592 A | 7/2000 | Adams et al. |
| 6,117,635 A | 9/2000 | Nazarenko et al. |
| 6,117,986 A | 9/2000 | Nardone et al. |
| 6,410,278 B1 | 6/2002 | Notomi et al. |
| 6,582,908 B2 | 6/2003 | Fodor et al. |
| 6,977,148 B2 | 12/2005 | Dean et al. |
| 7,476,736 B2 | 1/2009 | Kawa et al. |
| 7,504,111 B2 | 3/2009 | Fontana et al. |
| 7,790,386 B2 | 9/2010 | Ku et al. |
| 9,994,916 B2 | 6/2018 | Thornton et al. |
| 2005/0158768 A1 | 7/2005 | Kawa et al. |
| 2009/0131650 A1 | 5/2009 | Brahmasandra et al. |
| 2010/0009351 A1 | 1/2010 | Brahmasandra et al. |
| 2011/0182981 A1 | 7/2011 | Zhu |
| 2012/0141993 A1 | 6/2012 | Singhal et al. |

FOREIGN PATENT DOCUMENTS

| | | |
|---|---|---|
| EP | 0320308 A2 | 6/1989 |
| JP | 2007-514427 | 6/2007 |
| JP | 2009-533023 | 9/2009 |

OTHER PUBLICATIONS

Ausubel et al., Current Protocols in Molecular Biology, 3rd Ed. Wiley Interscience Publishers (1994); see Section 15; [Table of Contents Only].

Carroll et al., "Evaluation of the Abbott LCx Ligase Chain Reaction Assay for Detection of *Chlamydia trachomatis* and *Neisseria gonorrhoeae* in Urine and Genital Swab Specimens from a Sexually Transmitted Disease Clinic Population", J Clin Microbiol. (1998) 36(6): 1630-1633.

Chui et al., "A Comparison of three real-time PCR assays for the confirmation of *Neisseria gonorrhoeae* following detection of *N. gonorrhoeae* using Roche COBAS AMPLICOR", Clin Microbiol Infect. (2008) 14: 473-479.

Elghanian et al. "Selective Colorimetric Detection of Polynucleotides Based on the Distance-Dependent Optical Properties of Gold Nanoparticles." (1997) Science 277:1078-1081.

GenBank Accession No. AJ242839; "Neisseria gonorrhoeae DNA for opcA region, strain FA1090", Apr. 15, 2005; NCBI Database, National Library of Medicines (Bethesday, MD, USA) available via URL: www.ncbi.nih.gov/nuccore/AJ242839 in 7 pages.

Geraats-Peters et al., "Specific and Sensitive Detection of *Neisseria gonorrhoeae* in Clinical Specimens by Real-Time PCR", J Clin Microbiol. (2005) 43(11): 5653-5659.

Lizardi et al., "Exponential Amplification of Recombinant-RNA Hybridization Probes," BioTech. (Oct. 1988) 6: 1197-1202.

Marras S.A.E., "Selection of Fluorophore and Quenscher Pairs for Fluorescent Nucleic Acid Hybridization Probes", from *Methods in Molecular Biology: Fluorescent Energy Transfer Nucleic Acid Probes*, V.V. Didenko [Ed.]; Humana Press Inc., Totowa, NJ (2006); pp. 3-16.

(Continued)

*Primary Examiner* — Carla J Myers

(74) *Attorney, Agent, or Firm* — Knobbe, Martens, Olson & Bear, LLP

(57) ABSTRACT

Methods and compositions for detection of *Neisseria gonorrhoeae* are disclosed herein. In some embodiments, the presence or absence of *N. gonorrhoeae* in a sample is determined using nucleic acid-based testing methods using primers and/or probes that bind to opcA gene region of *N. gonorrhoeae*.

1 Claim, 12 Drawing Sheets

Specification includes a Sequence Listing.

(56) References Cited

OTHER PUBLICATIONS

Mitsuhashi et al., "Technical Report: Part 2. Basic Requirements for Designing Optimal PCR Primers", J Clin Lab Analys. (1996) 10:285-293.
Mullis et al., "Specific Synthesis of DNA in Vitro via a Polymerase-Catalyzed Chain Reaction", PCR; Meth Enzymol. (1987) 155: 335-350.
Newton et al. "Instrumentation, Reagents and Consumables." PCR, 2nd Ed., Springer-Verlag (New York: 1997), Chapter 2, p. 8-28.
Sambrook et al., "Molecular Cloning: A Laboratory Manual", 1989 Cold Spring Harbor Laboratory Press (Cover & Contents pages only) & pp. 14.15-14.16.
Whiley et al., "A real-time PCR assay for the detection of *Neisseria gonorrhoeae* by LightCycler", Diagn Microbiol Infect Disease (2002) 42: 85-89.
Whitcombe et al., "Detection of PCR products using self-probing amplicons and fluorescence", Nature (1999) 17:804-807.
Zhu et al., "Typing *Neisseria meningitidis* by Analysis of Restriction Fragment Length Polymorphisms in the Gene Encoding the Class 1 Outer Membrane Protein: Application to Assessment of Epidemics throughout the Last 4 Decades in China", J Clin Microbiol (1995) 33(2): 458-462.
Zhu et al., "The opcA and ψopcB regions in *Neisseria*: genes, pseudogenes, deletions, insertion elements and DNA islands", Mol Microbiol (1999) 33(3): 635-650.
Zhu et al., "Genetic analysis of conservation and variation of lipooligosaccharide expression in two L8-immunotype strains of *Neisseria meningitidis*", FEMS Microbiol Lett. (2001) 203: 173-177.
Zhu et al., "Immunologic and genetic characterization of lipooligosaccharide variants in a *Neisseria meningitidis* serogroup C strain", FEMS Immunol Med Microbiol. (2002) 34: 193-200.
Zhu et al., "Identification of opcA gene in *Neisseria polysaccharea*: Interspecies diversity of OPC protein family", Gene (2003) 307: 31-40.
International Search Report and Written Opinion dated Jul. 7, 2014 for Application No. PCT/US2014/021949, filed Mar. 7, 2014.
International Preliminary Report on Patentability dated Sep. 15, 2015 for Application No. PCT/US2014/021949, filed Mar. 7, 2014.

FIG. 1A  opcA-6 Primer locations in outer protein gene (opcA) gene, strain FA1090 (GenBank AJ242839) (SEQ ID NO:7)

```
Position: 1                                                                                           1420 bp
         10        20        30        40        50        60        70        80        90       100
5' gtccgaatcttgtgtcgacttccatcctgccctccaaggttaattttcaccactcaaacaaccgtaaccgtatcttcagttgatggtcgatatttta 100 aaaataaataatataacacaatagtattttgataaaattacctaacgagtacagacatgtattcagaaacaagcctaaacgcaccgtaaaatgaa 200 aaaatactggcagcctgcgcacCCTTTCCCTGTCCCTTTCTGcctgtacttcgactcaagtaacttcTTTTGTGAGGGACTCTCCGAGGgactcgtagatg 300
                                                                                    >gc.opca.d5> tCAGGGAAGCCTTTATCACAACaaaggcagaatcatatctgccccgtctcttcaggataagcaaatttcataaatcgtctcagaacgagcacaaaa 400
              <Gc.opca.rp5< aaattacaaagaaagaagaaaagaagcagactactaaattcagcatcgttattaaatgaatcaacatcagaagccctatctgcccttaaaaac 500 gctatcgtaattcctaaacgccctaaacgctccctggcaaaaaatataaaaacggtttcatcctgtaaaTACGTGTGCGGATGTGGAAgCTCGGTGGG 600
                                                                                       >gC.opCa.fp5>

CAAACGGAGCAATgaGAGATGTTAGGGACATAGAAAGGCTAATaagccgaaacgtcccttacgtcgtatcggagacgccattcaaaacatgtgcatgga 700
                                <gc.opCA.rp8<                                            <gc.opca.d6<

5' aaccaatgtgtccattaggatgtatcgccaggagtgccgttcagaatcgtcagatttttatgacgaaatgcttgagcatcacgagaatttcataggatcc 800
```

FIG. 1B   opcA-6 Primer locations in outer protein gene (opcA) gene, strain FA1090 (GenBank AJ242839) (SEQ ID NO:7)

Position: 1          10         20         30         40         50         60         70         80         90         100
         |          |          |          |          |          |          |          |          |          |          |
5' tccaaatcattcgatcatcacttcttccccttagcgttacaaactttacaacagacatggcgtgtactcccgatttaatctaatcacactccacaac
3'                                                                                                                      900

5' tccctatcaatataactgctacttctctgagtagtatcaaccaacctaacaaaggactaaaaatgaaaaagcactgcttgactgactattgccgc
3'                                                                                                                      1000

5' catctccggtactgcgtatggcccagttgcccgactttctgggtaaaggcgaatatacgtccgtacagacatctccaaacaaacgctgaaaaatgccgat
3'                                                                                                                      1100

5' ttgaaagaaaaacacaaagtacaaaaaaacatcggtttccgtccgatatgccgttttgacgatattcaccacggcatgcgtttcgaagtatcacacagcc
3'                                                                                                                      1200

5' gagacaaaaaagacatgtacgttgtgaccgaaagtactactaaccattcggcaaagacgttaaagaaaaacgcaccgacgtgtatgccggttacaccta
3'                                                                                                                      1300

5' cactcaaccgatcagtgaagccaccaagccgtgccgtttagtttgggctatgaaaataaaagatgcggtagctaatgagaaaggaacagtcagc
3'

|          |
| FIG. 1A  |
| FIG. 1B  |

| Neisseria gonorrhoeae Specificity Testing | | | |
|---|---|---|---|
| sample # | Organism | Strain/ ATCC #'s | Results |
| 1 | Neisseria gonorrhoeae | 53421 | + |
| 2 | Neisseria gonorrhoeae | 53424 | + |
| 3 | Neisseria gonorrhoeae | CHD5 | + |
| 4 | Neisseria gonorrhoeae | NGC0193 | + |
| 5 | Neisseria gonorrhoeae | NGC115 | + |
| 6 | Neisseria gonorrhoeae | NGC5 | + |
| 7 | Neisseria gonorrhoeae | NGC6 | + |
| 8 | Neisseria gonorrhoeae | 700717 | + |
| 9 | Neisseria gonorrhoeae | 700718 | + |
| 10 | Neisseria gonorrhoeae | 19424 | + |
| 11 | Neisseria gonorrhoeae | 53425 | + |
| 12 | Neisseria gonorrhoeae | 10150 | + |
| 13 | Neisseria gonorrhoeae | 43069 | + |
| 14 | Neisseria gonorrhoeae | 53423 | + |
| 15 | Neisseria gonorrhoeae | 23051 | + |
| 16 | Neisseria gonorrhoeae | 27628 | + |
| 17 | Neisseria gonorrhoeae | 27629 | + |
| 18 | Neisseria gonorrhoeae | 27633 | + |
| 19 | Neisseria gonorrhoeae | 31151 | + |
| 20 | Neisseria gonorrhoeae | 31397 | + |
| 21 | Neisseria gonorrhoeae | 31407 | + |
| 22 | Neisseria gonorrhoeae | 31953 | + |
| 23 | Neisseria gonorrhoeae | 53420 | + |
| 24 | Neisseria gonorrhoeae | 53422 | + |
| 25 | Neisseria gonorrhoeae | 6016178 | + |
| 26 | Neisseria gonorrhoeae | 728SPR | + |
| 27 | Neisseria gonorrhoeae | CLGJ4 | + |
| 28 | Neisseria gonorrhoeae | IU2254 | + |
| 29 | Neisseria gonorrhoeae | IU2265 | + |
| 30 | Neisseria gonorrhoeae | IU2266 | + |
| 31 | Neisseria gonorrhoeae | TC548 | + |
| 32 | Neisseria gonorrhoeae | IU2273 | + |
| 33 | Neisseria gonorrhoeae | IU24929 | + |
| 34 | Neisseria gonorrhoeae | IU330576 | + |
| 35 | Neisseria gonorrhoeae | BDSWE8658 | + |
| 36 | Neisseria gonorrhoeae | BDAR13 | + |

FIG. 2B

| | Neisseria gonorrhoeae Specificity Testing | | |
|---|---|---|---|
| sample # | Organism | Strain/ ATCC #'s | Results |
| 37 | Neisseria gonorrhoeae | BDAR150 | + |
| 38 | Neisseria gonorrhoeae | BDRGC3 | + |
| 39 | Neisseria gonorrhoeae | BDRGC6 | + |
| 40 | Neisseria gonorrhoeae | BDRGC9 | + |
| 41 | Neisseria gonorrhoeae | BDRGC12 | + |
| 42 | Neisseria gonorrhoeae | BDRGC13 | + |
| 43 | Neisseria gonorrhoeae | BDF28 | + |
| 44 | Neisseria gonorrhoeae | UCLA537 | + |
| 45 | Neisseria gonorrhoeae | BD4-11 | + |
| 46 | Neisseria gonorrhoeae | BD4-18 | + |
| 47 | Neisseria gonorrhoeae | UCLA949 | + |
| 48 | Neisseria gonorrhoeae | UCLA969 | + |
| 49 | Neisseria gonorrhoeae | UCLA1020 | + |
| 50 | Neisseria gonorrhoeae | BD9 | + |
| 51 | Neisseria gonorrhoeae | BD15 | + |
| 52 | Neisseria gonorrhoeae | 35542 | + |
| 53 | Neisseria gonorrhoeae | BD7 | + |
| 54 | Neisseria gonorrhoeae | 27632 | + |
| 55 | Neisseria gonorrhoeae | 27631 | + |
| 56 | Neisseria gonorrhoeae | 35201 | + |
| 57 | Neisseria gonorrhoeae | 35541 | + |
| 58 | Neisseria gonorrhoeae | 27630 | + |
| 59 | Neisseria gonorrhoeae | D4-05 | + |
| 60 | Neisseria gonorrhoeae | D4-11 | + |
| 61 | Neisseria gonorrhoeae | D4-17 | + |
| 62 | Neisseria gonorrhoeae | D4-08 | + |
| 63 | Neisseria gonorrhoeae | BDF18 | + |
| 64 | Neisseria gonorrhoeae | BDF45 | + |
| 65 | Neisseria gonorrhoeae | BD8658 | + |
| 66 | Neisseria gonorrhoeae | BD86-36238 | + |
| 67 | Neisseria gonorrhoeae | MAYO4844 | + |
| 68 | Neisseria gonorrhoeae | MHD2900 | + |
| 69 | Neisseria gonorrhoeae | WHO3 | + |
| 70 | Neisseria gonorrhoeae | WHO5 | + |
| 71 | Neisseria gonorrhoeae | WHO7 | + |
| 72 | Neisseria gonorrhoeae | UCLA493 | + |

FIG. 3A

| Specificity Testing non-gonorrhoeae Neisseria's (GC-opcA- 6) | | |
|---|---|---|
| Organism | Strains Tested | # Cross-React |
| Branhamella catarrhalis | 1 | 0 |
| Neisseria cinerea | 6 | 0 |
| Neisseria elongata | 1 | 0 |
| Neisseria flava | 2 | 0 |
| Neisseria flavescens | 3 | 0 |
| Neisseria lactamica | 9 | 0 |
| Neisseria meningitidis | 9 | 0 |
| Neisseria meningitidis A | 1 | 0 |
| Neisseria meningitidis B | 1 | 0 |
| Neisseria meningitidis C | 4 | 0 |
| Neisseria meningitidis D | 1 | 0 |
| Neisseria meningitidis Y | 1 | 0 |
| Neisseria meningitidis W135 | 1 | 0 |
| Neisseria mucosa | 3 | 0 |
| Neisseria perflava | 1 | 0 |
| Neisseria polysaccharea | 1 | 0 |
| Neisseria siccia | 3 | 0 |
| Neisseria subflava | 14 | 0 |
| Neisseria weaverii | 1 | 0 |

FIG. 3B

| Specificity Testing non-gonorrhoeae Neisseria's (GC-opcA- 6) | | |
|---|---|---|
| Organism | Strains Tested | # Cross-React |
| Neisseria gonorrhoeae | Yes | Yes |
| Branhamella catarrhalis | NO | NO |
| Neisseria cinerea | Yes | NO |
| Neisseria elongata | NO | NO |
| Neisseria flava | NO | NO |
| Neisseria flavescens | NO | NO |
| Neisseria lactamica | Yes | NO |
| Neisseria meningitidis | NO | NO |
| Neisseria meningitidis A | NO | NO |
| Neisseria meningitidis B | NO | NO |
| Neisseria meningitidis C | NO | NO |
| Neisseria meningitidis D | NO | NO |
| Neisseria meningitidis Y | NO | NO |
| Neisseria meningitidis W135 | NO | NO |
| Neisseria mucosa | NO | NO |
| Neisseria perflava | NO | NO |
| Neisseria polysaccharea | NO | NO |
| Neisseria siccia | Yes | NO |
| Neisseria subflava | NO | NO |
| Neisseria weaverii | NO | NO |

| FIG. 4A | FIG. 4B | FIG. 4C |

| Vaginal Panel | | |
|---|---|---|
| sample # | Organism | Results |
| 1 | Rahnella aquatilis | - |
| 2 | Enterobacter aerogenes | - |
| 3 | Campylobactor coli | - |
| 4 | Eikenella corrodens | - |
| 5 | Chromobacterium violaceum | - |
| 6 | Agrobacterium radiobacter | - |
| 7 | Escherichia coli | - |
| 8 | Proteus vulgaris | - |
| 9 | Acinetobactor baumannii | - |
| 10 | Klebsiella oxytoca | - |
| 11 | Kingnella dentrificans | - |
| 12 | Erysipelothrix rhusiopathiae | - |
| 13 | Actinomyces pyogenes | - |
| 14 | Corynebacterium genitalium biovar1 | - |
| 15 | Aerococcus viridans | - |
| 16 | Streptococcus sanguis | - |
| 17 | Streptococcus salivarius | - |
| 18 | Staphylococcus saprophyticus | - |
| 19 | Listeria monocytogenes | - |
| 20 | Enterococcus avium | - |
| 21 | Crytococcus neoformans | - |
| 22 | Enterococcus faecalis | - |
| 23 | Enterococcus faecium | - |
| 24 | Klebsiella ozaeneae | - |
| 25 | Proteus mirabilis | - |
| 26 | Salmonella cholerasuis | - |
| 27 | Salmonella typhimurium | - |
| 28 | Staphylococcus aureus, non-protein A | - |
| 29 | producing | - |
| 30 | Staphylococcus epidermidis | - |
| 31 | | - |
| 32 | Streptococcus pyofenes (Group A) | - |
| 33 | Streptococcus mitis | - |
| 34 | Streptococcus mitis | - |
| 35 | Streptococcus mutans | - |
| 36 | Strepococcus pneumoniae | - |
| 37 | Streptomyces griseus | - |
| 38 | Vibrio parahaemolyticus | - |
| 39 | Yersinia enterocolitica | - |
| 40 | Acinetobacter calcoaceticus | - |

FIG. 4B

| | Vaginal Panel | |
|---|---|---|
| sample # | Organism | Results |
| 41 | Acinetobacter lwoffi | - |
| 42 | Aeromonas hydrophilia | - |
| 43 | Alcaligenes faecalis | - |
| 44 | Bacillus subtilis | - |
| 45 | Candida albicans | - |
| 46 | Candida glabrata | - |
| 47 | Candida tropicalis | - |
| 48 | Citrobacter freundii | - |
| 49 | Corynebacterium renale | - |
| 50 | Edwardsiella tarda | - |
| 51 | Enterobacter cloacae | - |
| 52 | Flavobacterium meningosepticum | - |
| 53 | Gemella haemolysans | - |
| 54 | Haemophilus influenzae | - |
| 55 | Kingella kingae | - |
| 56 | Lactobacillus jensenii | - |
| 57 | Moraxella osloensis | - |
| 58 | Moraxella osloensis | - |
| 59 | Morganella monganii | - |
| 60 | Plesiomonas shigelloides | - |
| 61 | Providencia stuartii | - |
| 62 | Rhodococcus equi | - |
| 63 | Salmonella minnesota | - |
| 64 | Escherichia coli | - |
| 65 | Klebsiella pneumoniae | - |
| 66 | Streptococcus agalactiae (Group B) | - |
| 67 | Acinetobacter calcoaceticus | - |
| 68 | Candida glabrata | - |
| 69 | Gardnerella vaginalis | - |
| 70 | Serratia marcescens | - |
| 71 | Streptcoccus bovis | - |
| 72 | Corynebacterium xerosis | - |
| 73 | Peptostreptococcus anaerobius | - |
| 74 | E coli HPV 6 | - |
| 75 | E coli HPV 11 | - |
| 76 | E coli HPV 16 | - |
| 77 | E coli HPV 18 | - |
| 78 | Veillonella parvula | - |
| 79 | Clostridium perfringens | - |
| 80 | Lactobacillus acidophilus | - |

FIG. 4C

| | Vaginal Panel | |
|---|---|---|
| sample # | Organism | Results |
| 81 | Bacteroides fragilis | - |
| 82 | Peptostreptococcus anaerobius | - |
| 83 | Pseudomonas aeruginosa | - |
| 84 | Peptostreptococcus productus | - |
| 85 | Propionibacterium acnes | - |
| 86 | Pseudomonas fluorescens | - |
| 87 | Pseudomonas putida | - |
| 88 | Candida parapsilosis | - |
| 89 | Legionella pneumophilia | - |
| 90 | Mycobacterium smegmatis | - |
| 91 | Campylobacter jejuni | - |
| 92 | Mobiluncus mulieris | - |
| 93 | Actinomyces israelii | - |
| 94 | Lactobacillus brevis | - |
| 95 | Bifidobacterium adolescentis | - |
| 96 | Clostifium difficile | - |
| 97 | Atopobium vaginae | - |
| 98 | Anaerococcus vaginalis | - |
| 99 | Bifidobacterium infantis | - |
| 100 | Bifidobacterium brevis | - |
| 101 | Saccharomycesser cerevisiae | - |
| 102 | Micrococcus leutus | - |
| 103 | Leuconostoc paramensenteroides | - |
| 104 | Lactobacillus vaginalis | - |
| 105 | Bifidobacterium infantis | - |
| 106 | Bifidobacterium brevis | - |
| 107 | Saccharomyces cerevisiae | - |
| 108 | Micrococcus leutus | - |
| 109 | Leuconostoc paramensenteroides | - |
| 110 | Lactobacillus vaginalis | - |
| 111 | Bifidobacterium bifidium | - |
| 112 | Mobiluncus curtsii | - |
| 113 | Peptostreptococcus asaccharoyticus | - |
| 114 | Bacteroides ureoeolyticum | - |
| 115 | Achromobacter xerosis | - |
| 116 | Lactobacillus iners | - |

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
tacgtgtgcg gatgtggaa                                                19

<210> SEQ ID NO 2
<211> LENGTH: 27
<212> TYPE: DNA
<213> ORGANISM: Artificial Sequence
<220> FEATURE:
```

<223> OTHER INFORMATION: Synthetic oligonucleotide

<400> SEQUENCE: 2
ttagcctttc tatgtcccta acatctc                                    27

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
ctcggtgggc aaacggagca a                                          21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
cctttccctg tccctttctg                                            20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gttgtgataa aggcttcgct g                                          21

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
ccctcggaga gtccctcgac aaaa                                       24

<210> SEQ ID NO 7
<211> LENGTH: 1400
<212> TYPE: DNA
<213> ORGANISM: Neisseria gonorrhoeae

<400> SEQUENCE: 7
gtccgaatct tgtcatgcac ttccatcctg ccctccaagg ttaattttca ccactcaaac    60
aaccgtaacc ggtatcttca gttgatggtc ggatatttta aaataaata atataacaca   120 atagtatttt gataaaaatt tacctaacga ggtacagaca tgtattcaga aaacaagcct   180
aaacgcaccg taaaaatgaa aaaatactgg cagcctgcac cctttccctg tccctttctg   240
cctgtacttc gactcaagta acttcttttg tcgagggact ctccgaggga ctcgtagatg   300
tcagcgaagc ctttatcaca acaaaggcag aatcatattc tgccccgtct cttcaggata   360
agcaaatttt cataaatcgc gtctcagaac gagcacaaaa aaattacaaa gaaagaagga   420 aaagaaaga agcagactta ctaaattcag catcgttatt aaatgaatca acatcagaag   480
ccctatctgc ccttaaaaac gctatcgtaa ttcctaaacg ccctaaacgc tccttgggca   540

```
aaaaatataa aaacggtttt catcctgtaa atacgtgtgc ggatgtggaa gctcggtggg    600
caaacggagc aatgagagat gttagggaca tagaaaggct aataagccga aacgtccctt    660
tacgtcgtat cggagacgcc attcaaaaca tgtgcatgga aaccaatgtg tccattagga    720
tgtatcgcca ggagtgccgt tcagaatcgt cagattttta tgacgaaatg cttgagcatc    780
acgagaattt cataggatcc tccaaatcat tcgcatcatc acttcttccc cttagcgtta    840
caaactttac aacagacatg gcgtgtactc ccgaatttta atctaatcac actccacaac    900
tccctatcaa tataactgct acttctctga gtagtatcaa ccaaccctta acaaaggact    960
aaaaaatgaa aaaagcactg cttgcactga ctattgccgc catctccggt actgctatgg   1020
cccagttgcc cgactttctg ggtaaaggcg aatataccgt ccgtacagac atctccaaac   1080
aaacgctgaa aaatgccgat ttgaaagaaa aacacaaagt acaaaaaaac atcggtttcc   1140
gtgccgatat gccgtttgac gatattcacc acggcatgcg tttcgaagta tcacacagcc   1200
gagacaaaaa agacatgtac gttgtgaccg aaagtactac taaaccattc ggcaaagacg   1260
ttaaagaaaa acgcaccgac gtgtatgccg gttacaccta cactcaaccg atcagtgaag   1320
ccaccaaact gcgtgccggt ttaggtttgg gctatgaaaa atacaaagat gcggtagcta   1380
atgagaaagg aacagtcagc                                               1400
```

DETECTION OF *NEISSERIA GONORRHOEAES*

CROSS-REFERENCE TO RELATED APPLICATIONS

This application is a division of U.S. patent application Ser. No. 14/775,941, filed Sep. 14, 2015, now U.S. Pat. No. 9,994,916, which is a U.S. National Phase under 35 U.S.C. § 371 of International Application No. PCT/US2014/021949, filed Mar. 7, 2014, which claims priority to U.S. Provisional Patent Application No. 61/798,757, entitled "DETECTION OF *NEISSERIA GONORRHOEAES*," filed Mar. 15, 2013, the entire contents of each of which is hereby incorporated by reference.

REFERENCE TO SEQUENCE LISTING

The present application is being filed along with a Sequence Listing in electronic format. The Sequence Listing is provided as a file entitled SEQLISTING.TXT, created Mar. 15, 2013, which is 4 Kb in size. The information in the electronic format of the Sequence Listing is incorporated herein by reference in its entirety.

BACKGROUND

Field

The present disclosure relates to methods, compositions, primers, and probes for detection of *Neisseria gonorrhoeae*. More specifically, the present disclosure relates detection of *N. gonorrhoeae* by nucleic acid-based testing methods using primers and/or probes that bind to the major outer protein opcA gene region of *N. gonorrhoeae*. For example, these primers and probes can be used to amplify *N. gonorrhoeae* nucleic acids in biological samples to determine the presence of *N. gonorrhoeae* or to determine the presence of *N. gonorrhoeae* nucleic acids.

Description of the Related Art

*Neisseria gonorrhoeae* is a species of non-sport forming, non-motile, gram-negative diplococci bacteria responsible for gonorrhea, a bacterial infection of the lower genital tract that is transmitted mainly by sexual contact. Symptoms of infection with *N. gonorrhoeae* differ depending on the site of infection, and often time, the infections are asymptomatic. Gonorrhea infection can cause conjunctivitis, pharyngitis, proctitis or urethritis, prostatitis and orchitis. Ascending infection in women can also lead to the development of acute pelvic inflammatory disease, one of the leading causes of female infertility. Gonorrhea infection can pass from an infected mother to her baby during vaginal delivery, and can result in gonococcal conjunctivitis in the newborn's eyes.

*N. gonorrhoeae* is closely related genetically to *N. meningitidis* (meningococci), the causative agent of one type of bacterial meningitis, and slightly less related to *N. lactamica*, an occasional human pathogen. Both *N. gonorrhoeae* and *N. meningitidis* infect humans only. There are several additional species of *Neisseria* that may be considered normal flora in humans including *N. cinerea, N. elongata, N. flavescens, N. mucosa, N. sicca,* and *N. subflava*.

A number of nucleic acid amplification tests (NAATs) have been developed for clinical evaluation of *N. gonorrhoeae* infections, including Amplicor® CT/NG test targeting the cytosine DNA methyltransferase gene (Roche Diagnostic Corporation, Basel, Switzerland); ProbeTec™ Qx Amplification assay targeting the multi-copy pilin genes (Becton, Dickinson and Company, Franklin Lakes, N.J.); LCx® assay targeting opacity genes (opa) (Abbott Laboratories, Abbott Park, Ill.); and GenProbe APTIMA™ Combo 2 version of TMA targeting 16S ribosomal RNA gene (Gen-Probe, Incorporated, San Diego, Calif.). The NAATs have the advantage of detecting *N. gonorrhoeae* without pelvic examination or intraurethral swab specimen (for males) (e.g., by testing urine). However, the primers employed by certain NAATs for *N. gonorrhoeae* may cross-react with nongonococcal *Neisseria* species. Therefore, there is a need for a test that can detect *N. gonorrhoeae* with high sensitivity and reduced false positive results due to cross-reactivity with other bacterial species, such as *Neisseria* species.

SUMMARY

One aspect of the instant disclosure is related to probes and primers capable of hybridizing to the major outer protein gene (opcA). Some embodiments disclosed herein provide an oligonucleotide probe or primer up to about 100 nucleotides in length which is capable of hybridizing to the major outer protein gene (opcA) of *Neisseria gonorrhoeae*. In some embodiments, the probe or primer comprises a sequence selected from the group consisting of SEQ ID NOs: 1-6, or sequence that exhibits at least about 85% identity to a sequence selected from the group consisting of SEQ ID NOs: 1-6.

In some embodiments, the probe or primer consists a sequence selected from the group consisting of SEQ ID NOs: 1-6, or sequence that exhibits at least about 85% identity to a sequence selected from the group consisting of SEQ ID NOs: 1-6. In some embodiments, the probe or primer consists a sequence that exhibits at least about 95% identity to a sequence selected from the group consisting of SEQ ID NOs: 1-6. In some embodiments, the probe or primer is consisting of a sequence selected from the group consisting of SEQ ID NOs: 1-6.

Another aspect of the instant disclosure is related to methods for detecting the presence of opcA sequence from *Neisseria gonorrhoeae* in a biological sample. Some embodiments disclosed herein provide a method to determine the presence of a major outer protein gene (opcA) sequence from *Neisseria gonorrhoeae* in a biological sample, where the method comprises: contacting the biological sample with at least one pair of primers capable of hybridizing to the major outer protein gene (opcA) of *Neisseria gonorrhoeae*, wherein each primer in the at least one pair of primers comprises a sequence selected from the group consisting of SEQ ID NOs: 1-6, or sequence that exhibits at least about 85% identity to a sequence selected from the group consisting of SEQ ID NOs: 1-6, and wherein the at least one pair of primers is configured to generate an amplicon of an opcA sequence under standard nucleic acid amplification conditions; generating an amplicon of the opcA sequence from the biological sample, if the sample comprises *Neisseria gonorrhoeae*; and determining the presence or amount of one or more amplified products as an indication of the presence of the opcA sequence in the biological sample.

In some embodiments, the biological sample is a clinical sample. In some embodiments, the biological sample is collected from the urethra, penis, anus, throat, cervix, or vagina. In some embodiments, the biological sample is a vaginal sample.

In some embodiments, the biological sample is contacted with one pair of primers. In some embodiments, the one pair of primers is: a) SEQ ID NOs: 1 and 2; or b) SEQ ID NOs: 4 and 5.

In some embodiments, the amplification is carried out using a method selected from the group consisting of polymerase chain reaction (PCR), ligase chain reaction (LCR), loop-mediated isothermal amplification (LAMP), strand displacement amplification (SDA), replicase-mediated amplification, Immuno-amplification, nucleic acid sequence based amplification (NASBA), self-sustained sequence replication (3SR), rolling circle amplification, and transcription-mediated amplification (TMA).

In some embodiments, the PCR is selected from the group consisting of Real-Time PCR, End-Point PCR, AFLP, Alu-PCR, Asymmetric PCR Colony PCR, DD-PCR, Degenerate PCR, Hot-start PCR, In situ PCR, Inverse PCR, Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Repetitive extragenic palindromic-PCR (Rep-PCR), reverse transcriptase PCR (RT-PCR), TAIL-PCR, Touchdown PCR and Vectorette PCR. In some embodiments, the PCR is quantitative real-time PCR (QRT-PCR).

In some embodiments, each primer comprises exogenous nucleotide sequence which allows post-amplification manipulation of amplification products without a significant effect on amplification itself.

In some embodiments, each primer in the primer pair is flanked by complementary sequences comprising a fluorophore at the 5' end, and a fluorescence quencher at the 3' end.

Yet another respect of the instant disclosure is related to compositions for the detection of *Neisseria gonorrhoeae* sequences. Some embodiments disclosed herein provide a composition for the detection of *Neisseria gonorrhoeae*, where the composition comprises: a first and a second amplification primers specifically hybridize to the sequence of the major outer protein gene (opcA) of *Neisseria gonorrhoeae* or the complement thereof, wherein the first and the second amplification primers are about 10 to about 50 nucleotides in length, and wherein the opcA has the nucleotide sequence of SEQ ID NO: 7.

In some embodiments, the composition further comprises a probe, wherein the probe specifically hybridizes to an opcA amplicon.

In some embodiments, the probe comprises a sequence of SEQ ID NO: 3 or 6, or sequence that exhibits at least about 85% identity to a sequence of SEQ ID NO: 3 or 6. In some embodiments, the probe has a sequence of SEQ ID NO: 3 or SEQ ID NO: 6.

In some embodiments, the probe comprises a fluorescence emitter moiety and a fluorescence quencher moiety.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 shows the sequence of an opcA gene region in *N. gonorrhoeae* strain FA1090 (SEQ ID NO: 7). Also shown are the locations of various primers and probes disclosed in the embodiments described herein.

FIGS. 3A-B show the specificity testing results of the opcA-6 qPCR system for non-gonorrhoeae *Neisseria*.

FIGS. 4A-C show the specificity testing results of the opcA-6 qPCR system for organisms commonly found in vaginal clinical samples

DETAILED DESCRIPTION

Figure 2:
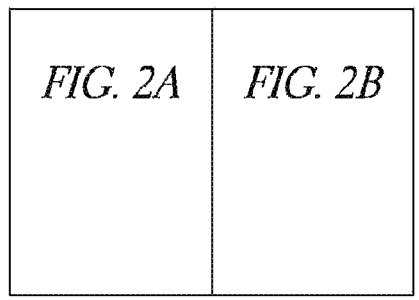
FIGS. 2A-B show the detection results of 72 *N. gonorrhoeae* clinical isolates using the opcA-6 qPCR system.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

Provided herein are methods and compositions for the detection of *N. gonorrhoeae* using primers and/or probes that bind to the major outer protein gene opcA of *N. gonorrhoeae*. These primers and probes can be used to amplify *N. gonorrhoeae* nucleic acids in biological samples to determine the presence or absence of *N. gonorrhoeae* in a sample, such as a biological sample. In addition, these primers and probes can be used to quantify the amount of *N. gonorrhoeae* nucleic acids in the sample.

Definitions

As used herein, a "nucleic acid" refers to a polymeric compound comprising nucleosides or nucleoside analogs which have nitrogenous heterocyclic bases, or base analogs, linked together by nucleic acid backbone linkages (e.g., phosphodiester bonds) to form a polynucleotide. Non-limiting examples of nucleic acid include RNA, DNA, and analogs thereof. The nucleic acid backbone can include a variety of linkages, for example, one or more of sugar-phosphodiester linkages, peptide-nucleic acid bonds, phosphorothioate or methylphosphonate linkages or mixtures of such linkages in a single oligonucleotide. Sugar moieties in the nucleic acid can be either ribose or deoxyribose, or similar compounds with known substitutions. Conventional nitrogenous bases (e.g., A, G, C, T, U), known base analogs (e.g., inosine), derivatives of purine or pyrimidine bases and "abasic" residues (i.e., no nitrogenous base for one or more backbone positions) are included in the term nucleic acid. That is, a nucleic acid can include only conventional sugars, bases and linkages found in RNA and DNA, or include both conventional components and substitutions (e.g., conventional bases and analogs linked via a methoxy backbone, or conventional bases and one or more base analogs linked via an RNA or DNA backbone).

As used herein, the term "isolate nucleic acids" refers to the purification of nucleic acids from one or more cellular components. The skilled artisan will appreciate that samples processed to "isolate nucleic acids" therefrom can include components and impurities other than nucleic acids. Samples that comprise isolated nucleic acids can be prepared from specimens using any acceptable method known in the art. For example, cells can be lysed using known lysis agents, and nucleic acids can be purified or partially purified from other cellular components. Suitable reagents and protocols for DNA and RNA extractions can be found in, for example, U.S. Patent Application Publication Nos. US 2010-0009351, and US 2009-0131650, respectively (each of which is incorporated herein by reference in its entirety). In nucleic acid testing (e.g., amplification and hybridization methods discussed in further detail below), the extracted nucleic acid solution can be added directly to a reagents (e.g., either in liquid, bound to a substrate, in lyophilized form, or the like, as discussed in further detail below), required to perform a test according to the embodiments disclosed herein.

As used herein, "template" refers to all or part of a polynucleotide containing at least one target nucleotide sequence.

As used herein, a "primer" refers to a polynucleotide that can serve to initiate a nucleic acid chain extension reaction. The length of a primer can vary, for example, from about 5 to about 100 nucleotides, from about 10 to about 50 nucleotides, from about 15 to about 40 nucleotides, or from about 20 to about 30 nucleotides. The length of a primer can be about 10 nucleotides, about 20 nucleotides, about 25 nucleotides, about 30 nucleotides, about 35 nucleotides, about 40 nucleotides, about 50 nucleotides, about 75 nucleotides, about 100 nucleotides, or a range between any two of these values. In some embodiments, the primer has a length of 10 to about 50 nucleotides, i.e., 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49, 50, or more nucleotides.

As used herein, a "probe" refers to a nucleic acid oligomer that hybridizes specifically to a target sequence in a nucleic acid, under conditions that allow hybridization, thereby allowing detection of the target sequence or amplified nucleic acid. A probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe. Sequences are "sufficiently complementary" if they allow stable hybridization in appropriate hybridization conditions of a probe oligomer to a target sequence that is not completely complementary to the probe's target-specific sequence. The length of a probe can vary, for example, from about 5 to about 100 nucleotides, from about 10 to about 50 nucleotides, from about 15 to about 40 nucleotides, or from about 20 to about 30 nucleotides. The length of a probe can be about 10 nucleotides, about 20 nucleotides, about 25 nucleotides, about 30 nucleotides, about 35 nucleotides, about 40 nucleotides, about 50 nucleotides, about 100 nucleotides, or a range between any two of these values. In some embodiments, the probe has a length of 10 to about 50 nucleotides. 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49, 50, or more nucleotides.

In some embodiments, the probe can non-sequence specific. For example, in some embodiments, Preferably, the oligonucleotide primers and/or probes disclosed herein can be between 8 and 45 nucleotides in length. For example, the primers and or probes can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length.

The primer and probe sequences disclosed herein can be modified to contain additional nucleotides at the 5' or the 3' terminus, or both. The skilled artisan will appreciate that additional bases to the 3' terminus of amplification primers (not necessarily probes) are generally complementary to the template sequence. The primer and probe sequences disclosed herein can also be modified to remove nucleotides at the 5' or the 3' terminus. The skilled artisan will appreciate that in order to function for amplification, the primers or probes will be of a minimum length and annealing temperature as disclosed herein.

Oligonucleotide primers and probes can bind to their targets at an annealing temperature, which is a temperature less than the melting temperature ($T_m$). As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+ 0.41\times(G+C)\%-6-50/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)× 4° C.]. See, e.g., C. R. Newton et al. PCR, 2nd ed., Springer-Verlag (New York: 1997), p. 24. Other more sophisticated computations exist in the art, which take structural as well as sequence characteristics into account for the calculation of $T_m$. The melting temperature of an oligonucleotide can depend on complementarity between the oligonucleotide primer or probe and the binding sequence, and on salt conditions. In some embodiments, an oligonucleotide primer or probe provided herein has a $T_m$ of less than about 90° C. in 50 mM KCl, 10 mM Tris-HCl buffer, for example about 89° C., 88, 87, 86, 85, 84, 83, 82, 81, 80 79, 78, 77, 76, 75, 74, 73, 72, 71, 70, 69, 68, 67, 66, 65, 64, 63, 62, 61, 60, 59, 58, 57, 56, 55, 54, 53, 52, 50, 49, 48, 47, 46, 45, 44, 43, 42, 41, 40, 39° C., or less, including ranges between any two of the listed values.

In some embodiments, the primers disclosed herein, e.g., amplification primers, can be provided as an amplification primer pair, e.g., comprising a forward primer and a reverse primer (first amplification primer and second amplification primer). Preferably, the forward and reverse primers have $T_m$'s that do not differ by more than 10° C., e.g., that differ by less than 10° C., less than 9° C., less than 8° C., less than 7° C., less than 6° C., less than 5° C., less than 4° C., less than 3° C., less than 2° C., or less than 1° C.

The primer and probe sequences may be modified by having nucleotide substitutions (relative to the target sequence) within the oligonucleotide sequence, provided that the oligonucleotide contains enough complementarity to hybridize specifically to the target nucleic acid sequence. In this manner, at least 1, 2, 3, 4, or up to about 5 nucleotides can be substituted. As used herein, the term "complementary" refers to sequence complementarity between regions of two polynucleotide strands or between two regions of the same polynucleotide strand. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Fully complementary" refers to a first polynucleotide that is 100% or "fully" complementary to a second polynucleotide and thus forms a base pair at every nucleotide position. "Partially complementary" also refers to a first polynucleotide that is not 100% complementary (e.g., 90%, or 80% or 70% complementary) and contains mismatched nucleotides at one or more nucleotide positions. In some embodiments, an oligonucleotide includes a universal base.

As used herein, an "exogenous nucleotide sequence" refers to a sequence introduced by primers or probes used for amplification, such that amplification products will contain exogenous nucleotide sequence and target nucleotide sequence in an arrangement not found in the original template from which the target nucleotide sequence was copied.

As used herein, "sequence identity" or "percent identical" as applied to nucleic acid molecules is the percentage of nucleic acid residues in a candidate nucleic acid molecule sequence that are identical with a subject nucleic acid molecule sequence, after aligning the sequences to achieve the maximum percent identity, and not considering any nucleic acid residue substitutions as part of the sequence identity. Nucleic acid sequence identity can be determined using any method known in the art, for example CLUST-ALW, T-COFFEE, BLASTN.

As used herein, the term "sufficiently complementary" refers to a contiguous nucleic acid base sequence that is capable of hybridizing to another base sequence by hydrogen bonding between a series of complementary bases. Complementary base sequences can be complementary at each position in the oligomer sequence by using standard base pairing (e.g., G:C, A:T or A:U) or can contain one or more residues that are not complementary (including abasic positions), but in which the entire complementary base sequence is capable of specifically hybridizing with another base sequence in appropriate hybridization conditions. Contiguous bases can be at least about 80%, at least about 85%, at least about 90%, at least about 95%, at least about 99%, or 100% complementary to a sequence to which an oligomer is intended to hybridize. Substantially complementary sequences can refer to sequences ranging in percent identity from 100, 99, 98, 97, 96, 95, 94, 93, 92, 91, 90, 89, 88, 87, 86, 85, 84, 83, 82, 81, 80, 75, 70 or less, or any number in between, compared to the reference sequence. A skilled artisan can readily choose appropriate hybridization conditions which can be predicted based on base sequence composition, or be determined by using routine testing (see e.g., Sambrook et al., Molecular Cloning, A Laboratory Manual, $2^{nd}$ ed. (Cold Spring Harbor Laboratory Press, Cold Spring Harbor, N.Y., 1989).

Oligonucleotides

OpcA is a major outer protein gene present in *N. gonorrhoeae*. In *N. gonorrhoeae*, the nucleotide sequences of the opcA gene were first determined from two reference strains FA1090 and MS11 (Zhu et al., FEMS Immunol. Med. Microbiol. 193-200 (2002)). Three polymorphic sites, two synonymous mutations and one non-synonymous mutation, differed between the opcA of the two gonococcal strains, and a one codon deletion was found in MS11 opcA. Twenty-six strains of *N. gonorrhoeae* were examined by PCR using gonococcal opcA primer pairs, and opcA was found to be present in all these twenty-six gonococcal strains (Zhu et al., J. Clin. Microbiol., 458-62 (1995); Zhu et al., 2002). Fifty-one *N. gonorrhoeae* strains were also examined for opcA by PCR and DNA hybridization, and all strains showed presence of opcA in their genomes. Zhu et al., FEMS Microbiol. Lett. 173-77 (2001). The PCR products from the opcA gene were digested using four frequent-cutting restriction endonucleases (PCR-RFLP). The same PCR-RFLP patterns as that of reference strain FA1090 were observed in all gonococcal strains tested, showing conserved sequence of the opcA gene in *N. gonorrhoeae*.

Some embodiments disclosed herein provide oligonucleotides (e.g., amplification primers and probes) that are capable of specifically hybridizing (e.g., under standard nucleic acid amplification conditions, e.g., standard PCR conditions, and/or stringent hybridization conditions) to the opcA gene region in *N. gonorrhoeae*, or complement thereof. An exemplary sequence of the opcA gene region related to the embodiments disclosed herein is provided in GenBank Accession No. AJ242839. An exemplary sequence of the opcA gene region is provided in SEQ ID NO: 7. In some embodiments, primers and probes that specifically bind to the opcA gene region of *N. gonorrhoeae* (e.g., SEQ ID NO: 7) are used in detection of the presence or amount of *N. gonorrhoeae* nucleic acid in a biological sample. In some embodiments, provided is a primer that hybridizes to SEQ ID NO: 7 under standard conditions for nucleic acid amplification. Examples of oligonucleotide capable of specifically hybridizing to the opcA gene region in *N. gonorrhoeae* include, but are not limited, SEQ ID NOs: 1-6 as provided in Table 1. In Table 1, "oligo location" refers to the location of each oligonucleotide in SEQ ID NO: 7.

TABLE 1

| System Name | Oligo Name | Oligo Size | Oligo Location | Amplicon size (bp) | Sequence (5'-3') | Oligo Tm |
|---|---|---|---|---|---|---|
| opcA-6 | GC.opcA.FP6 | 19 | 572-590 | 74 | TACGTGTGCGGATGTGGAA (SEQ ID NO: 1) | 58 |
| | GC.opcA.RP6 | 27 | 616-642 | | TTAGCCTTTCTATGTCCCTA ACATCTC (SEQ ID NO: 2) | 58 |
| | GC.opcA.D6 | 21 | 592-612 | | CTCGGTGGGCAAACGGAGC AA (SEQ ID NO: 3) | 68 |
| opcA-5 | GC.opcA.FP5 | 20 | 221-240 | 102 | CCTTTCCCTGTCCCTTTCTG (SEQ ID NO: 4) | 55 |
| | GC.opcA.RP5 | 21 | 302-322 | | GTTGTGATAAAGGCTTCGC TG (SEQ ID NO: 5) | 54 |

TABLE 1-continued

| System Name | Oligo Name | Oligo Size | Oligo Location | Amplicon size (bp) | Sequence (5'-3') | Oligo Tm |
|---|---|---|---|---|---|---|
| | GC.opcA.D5 | 24 | 266-289 | | CCCTCGGAGAGTCCCTCGA CAAAA (SEQ ID NO: 6) | 62 |

Also provided herein are oligonucleotides containing 1, 2, 3, 4 or more mismatches or universal nucleotides relative to SEQ ID NOs: 1-6 or the complement thereof, including oligonucleotides that are at least 80% identical (for example at least 81%, 82%, 83%, 84%, 85%, 86%, 87%, 88%, 89%, 90%, 91%, 92%, 93%, 94%, 95%, 96%, 97%, 98%, 99% or 100% identical) to SEQ ID NOs: 1-6 or the complement thereof. In some embodiments, the oligonucleotide comprises a sequence selected from SEQ ID NO: 1-6. In some embodiments, the oligonucleotide comprises a sequence that is at least about 85% identity to a sequence selected from SEQ ID NO: 1-6. In some embodiments, the oligonucleotide consists a sequence selected from SEQ ID NO: 1-6. In some embodiments, the oligonucleotide consists a sequence that is at least about 85% identity or at least about 95% identity to a sequence selected from SEQ ID NO: 1-6.

Also disclosed herein are compositions that comprise the oligonucleotides (e.g., amplification primers and/or probes) that are capable of specifically hybridizing to the sequence of opcA gene region of *N. gonorrhoeae*. For example, the composition can comprise one or more amplification primers and/or one or more probes capable of specifically hybridizing to the sequence of opcA gene region of *N. gonorrhoeae*. In some embodiments, the composition comprises a first and second amplification primers capable of specifically hybridizing to the sequence of opcA gene region of *N. gonorrhoeae*. In some embodiments, the primer comprises a sequence of SEQ ID NO: 1, 2, 4, or 5. In some embodiments, the primer comprises a sequence that is at least about 85% identity or at least about 95% identity to a sequence of SEQ ID NO: 1, 2, 4, or 5. In some embodiments, the primer consists a sequence of SEQ ID NO: 1, 2, 4, or 5. In some embodiments, the primer consists a sequence that is at least about 85% identity or at least about 95% identity to a sequence of SEQ ID NO: 1, 2, 4, or 5.

In some embodiments, the composition further comprises a probe capable of specifically hybridizing to an opcA amplicon. In some embodiments, the probe comprises a sequence of SEQ ID NO: 3 or 6. In some embodiments, the probe comprises a sequence that is at least about 85% identity or at least about 95% identity to a sequence of SEQ ID NO: 3 or 6. In some embodiments, the probe consists a sequence of SEQ ID NO: 3 or 6. In some embodiments, the probe consists a sequence that is at least about 85% identity or at least about 95% identity to a sequence of SEQ ID NO: 3 or 6.

In some embodiments, oligonucleotide probes can include a detectable moiety. For example, in some embodiments, the oligonucleotide probes disclosed herein can comprise a radioactive label. Non-limiting examples of radioactive labels include $^3$H, $^{14}$C, $^{32}$P, and $^{35}$S. In some embodiments, oligonucleotide probes can include one or more non-radioactive detectable markers or moieties, including but not limited to ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe. For example, oligonucleotide probes labeled with one or more dyes, such that upon hybridization to a template nucleic acid, a detectable change in fluorescence is generated. While non-specific dyes may be desirable for some applications, sequence-specific probes can provide more accurate measurements of amplification. One configuration of sequence-specific probe can include one end of the probe tethered to a fluorophore, and the other end of the probe tethered to a quencher. When the probe is unhybridized, it can maintain a stem-loop configuration, in which the fluorophore is quenched by the quencher, thus preventing the fluorophore from fluorescing. When the probe is hybridized to a template nucleic sequence, it is linearized, distancing the fluorophore from the quencher, and thus permitting the fluorophore to fluoresce. Another configuration of sequence-specific probe can include a first probe tethered to a first fluorophore of a FRET pair, and a second probe tethered to a second fluorophore of a FRET pair. The first probe and second probe can be configured to hybridize to sequences of an amplicon that are within sufficient proximity to permit energy transfer by FRET when the first probe and second probe are hybridized to the same amplicon.

In some embodiments, the sequence specific probe comprises an oligonucleotide as disclosed herein conjugated to a fluorophore. In some embodiments, the probe is conjugated to two or more flurophores. Examples of fluorophores include: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, CAL fluor orange, and the like.

In some embodiments, the probe is conjugated to a quencher. A quencher can absorb electromagnetic radiation and dissipate it as heat, thus remaining dark. Example quenchers include Dabcyl, NFQ's, such as BHQ-1 or BHQ-2 (Biosearch), IOWA BLACK FQ (IDT), and IOWA BLACK RQ (IDT). In some embodiments, the quencher is selected to pair with a fluorphore so as to absorb electromagnetic radiation emitted by the fluorophore. Flourophore/quencher pairs useful in the compositions and methods disclosed herein are well-known in the art, and can be found, e.g., described in S. Marras, "Selection of Fluorophore and Quencher Pairs for Fluorescent Nucleic Acid Hybridization Probes" available at the world wide web site molecular-beacons.org/download/marras,mmb06%28335%293.pdf.

In some embodiments, a fluorophore is attached to a first end of the probe, and a quencher is attached to a second end of the probe. Attachment can include covalent bonding, and can optionally include at least one linker molecule positioned between the probe and the fluorophore or quencher. In some embodiments, a fluorophore is attached to a 5' end of a probe, and a quencher is attached to a 3' end of a probe. In some embodiments, a fluorophore is attached to a 3' end of a probe, and a quencher is attached to a 5' end of a probe. Examples of probes that can be used in quantitative nucleic acid amplification include molecular beacons, SCORPION™ probes (Sigma), TAQMAN™ probes (Life Technologies) and the like. Other nucleic acid detection technologies that are useful in the embodiments disclosed herein include, but are not limited to nanoparticle probe technology (See, Elghanian, et al. (1997) *Science* 277:1078-1081) and Amplifluor probe technology (See, U.S. Pat. Nos. 5,866,366; 6,090,592; 6,117,635; and 6,117,986).

The nucleic acids provided herein can be in various forms. For example, in some embodiments, the nucleic acids are dissolved (either alone or in combination with various other nucleic acids) in solution, for example buffer. In some embodiments, nucleic acids are provided, either alone or in combination with other isolated nucleic acids, as a salt. In some embodiments, nucleic acids are provided in a lyophilized form that can be reconstituted. For example, in some embodiments, the isolated nucleic acids disclosed herein can be provided in a lyophilized pellet alone, or in a lyophilized pellet with other isolated nucleic acids. In some embodiments, nucleic acids are provided affixed to a solid substance, such as a bead, a membrane, or the like. In some embodiments, nucleic acids are provided in a host cell, for example a cell line carrying a plasmid, or a cell line carrying a stably integrated sequence.

Methods

Provided herein are methods for the detection and/or quantification of *N. gonorrhoeae* in a sample. In some embodiments, the method includes a step of contacting the sample to be analyzed with one or more oligonucleotides that specifically hybridize to the sequence of opcA gene region of *N. gonorrhoeae* under standard nucleic acid amplification conditions and/or stringent hybridization conditions. In some embodiments, the method includes generating an amplicon of the opcA sequence from the sample, if the sample comprises *N. gonorrhoeae*. The method can also include a step of determining the presence or amount of one or more amplified products as an indication of the presence of the opcA sequence and/or *N. gonorrhoeae* in the sample.

Nucleic Acid Testing

The methods described herein can include, for example, nucleic acid testing. For example, the test can include testing for target nucleic acid sequences in a sample. Various forms of nucleic acid testing can be used in the embodiments disclosed herein, including but not limited to, testing that involves nucleic acid amplification.

As used herein, nucleic acid amplification refers to any known procedure for obtaining multiple copies of a target nucleic acid sequence or its complement or fragments thereof, using sequence-specific methods. Examples of known amplification methods include, but are not limited to, polymerase chain reaction (PCR), ligase chain reaction (LCR), loop-mediated isothermal amplification (LAMP), strand displacement amplification (SDA) (e.g., multiple displacement amplification (MDA)), replicase-mediated amplification, immuno-amplification, nucleic acid sequence based amplification (NASBA), self-sustained sequence replication (3SR), rolling circle amplification, and transcription-mediated amplification (TMA). See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Dean et al, "Multiple displacement amplification," U.S. Pat. No. 6,977,148; Notomi et al., "Process for Synthesizing Nucleic Acid," U.S. Pat. No. 6,410,278; Landegren et al. U.S. Pat. No. 4,988,617 "Method of detecting a nucleotide change in nucleic acids"; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; Lizardi et al., BioTechnology, 6:1197 (1988); Lizardi et al., U.S. Pat. No. 5,854,033 "Rolling circle replication reporter systems." In some embodiments, two or more of the aforementioned nucleic acid amplification methods can be performed, for example sequentially.

For example, LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.).

PCR is a method well-known in the art for amplification of nucleic acids. PCR involves amplification of a target sequence using two or more extendable sequence-specific oligonucleotide primers that flank the target sequence. The nucleic acid containing the target sequence of interest is subjected to a program of multiple rounds of thermal cycling (denaturation, annealing and extension) in the presence of the primers, a thermostable DNA polymerase (e.g., Taq polymerase) and various dNTPs, resulting in amplification of the target sequence. PCR uses multiple rounds of primer extension reactions in which complementary strands of a defined region of a DNA molecule are simultaneously synthesized by a thermostable DNA polymerase. At the end of each cycle, each newly synthesized DNA molecule acts as a template for the next cycle. During repeated rounds of these reactions, the number of newly synthesized DNA strands increases exponentially such that after 20 to 30 reaction cycles, the initial template DNA will have been replicated several thousand-fold or million-fold. Methods for carrying out different types and modes of PCR are thoroughly described in the literature, for example in "PCR Primer: A Laboratory Manual" Dieffenbach and Dveksler, eds. Cold Spring Harbor Laboratory Press, 1995, and by Mullis et al. in patents (e.g., U.S. Pat. Nos. 4,683,195, 4,683,202 and 4,800,159) and scientific publications (e.g. Mullis et al. 1987, Methods in Enzymology, 155:335-350) where the contents of each reference are hereby incorporated by reference in their entireties.

PCR can generate double-stranded amplification products suitable for post-amplification processing. If desired, amplification products can be detected by visualization with agarose gel electrophoresis, by an enzyme immunoassay format using probe-based colorimetric detection, by fluorescence emission technology, or by other detection means known to one of skill in the art.

A wide variety of PCR methods have been described in many sources, for example, Ausubel et al. (eds.), Current Protocols in Molecular Biology, Section 15, John Wiley & Sons, Inc., New York (1994). Examples of PCR method include, but not limited to, Real-Time PCR, End-Point PCR, Amplified fragment length polymorphism PCR (AFLP-PCR), Alu-PCR, Asymmetric PCR, Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR.

Real-time PCR, also called quantitative real time polymerase chain reaction (QRT-PCR), can be used to simultaneously quantify and amplify a specific part of a given nucleic acid molecule. It can be used to determine whether a specific sequence is present in the sample; and if it is present, the number of copies of the sequence that are present. The term "real-time" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with fluorescence resonance energy transfer (FRET) probes measures fluorescent dye signal changes from cycle-to-cycle, preferably minus any internal control signals. The real-time procedure follows the general pattern of PCR, but the nucleic acid is quantified after each round of amplification. Two examples of method of quantification are the use of fluorescent dyes (e.g., SYBRGreen) that intercalate into double-stranded DNA, and modified DNA oligonucleotide probes that fluoresce when hybridized with a complementary DNA. Intercalating agents have a relatively low fluorescence when unbound, and a relatively high fluorescence upon binding to double-stranded nucleic acids. As such, intercalating agents can be used to monitor the accumulation of double strained nucleic acids during a nucleic acid amplification reaction. Examples of such non-specific dyes useful in the embodiments disclosed herein include intercalating agents such as SYBR Green I (Molecular Probes), propidium iodide, ethidium bromide, and the like.

Because of the specific target sequences, primers and probes, the methods disclosed herein can be used to detect the presence/absence or amount of N. gonorrhoeae in a sample with high sensitivity and accuracy. For example, the methods can accurately detect N. gonorrhoeae to the exclusion of closely-related non-gonorrhoeae Neisseria species. The methods have improved specificity, i.e., reduced or no cross-reactivity to closely-related non-gonorrhoeae Neisseria species (e.g., N. lactamica, N. cineria, and N. sicca), as compared to Pilin gene-based detection system (for example, ProbeTec™ Qx Amplification assay).

The primers disclosed herein can be paired with additional PCR systems using a uniform chemistry and thermal PCR profile to provide a panel of assays for the detection of vaginal organisms, to improve overall assay sensitivity and robustness.

In some embodiments, the oligonucleotide comprises a detectable moiety, as described herein, and the specific hybridization of the oligonucleotide to the opcA gene region can be detected, e.g., by direct or indirect means. Accordingly, some embodiments for the detection and/or identification of N. gonorrhoeae in a sample include the steps of providing a test sample; and contacting the sample with an oligonucleotide probe that specifically hybridizes to opcA gene region of N. gonorrhoeae under standard nucleic acid amplification conditions and/or stringent hybridization conditions, wherein the oligonucleotide probe is between about 10 and about 45 nucleotides in length, and comprises a detectable moiety, wherein the contacting is performed under conditions allowing for the specific hybridization of the primer to the opcA gene region if N. gonorrhoeae is present in the sample. The presence and/or amount of probe that is specifically bound to the opcA gene region (if present in the sample being tested) can be determined, wherein bound probe is indicative of the presence of N. gonorrhoeae in the sample. In some embodiments, the amount of bound probe is used to determine the amount of N. gonorrhoeae in the sample.

The determining step can be achieved using any methods known to those skilled in the art, including but not limited to, in situ hybridization, following the contacting step. The detection of hybrid duplexes (i.e., of a probe specifically bound to the opcA gene region) can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample. Those skilled in the art will appreciate that wash steps may be employed to wash away excess sample/target nucleic acids or oligonucleotide probe (as well as unbound conjugate, where applicable). Further, standard heterogeneous assay formats are suitable for detecting the hybrids using the labels present on the oligonucleotide primers and probes.

In some embodiments, a sample to be tested for the presence of N. gonorrhoeae is processed prior to performing the methods disclosed herein. For example, in some embodiments, the sample can be isolated, concentrated, or subjected to various other processing steps prior to performing the methods disclosed herein. For example, in some embodiments, the sample can be processed to isolate nucleic acids from the sample prior to contacting the sample with the oligonucleotides, as disclosed herein. In some embodiments, the methods disclosed herein are performed on the sample without culturing the sample in vitro. In some embodiments, the methods disclosed herein are performed on the sample without isolating nucleic acids from the sample prior to contacting the sample with oligonucleotides as disclosed herein.

The methods disclosed herein are amendable to automation, thereby providing a high-throughput option for the detection of N. gonorrhoeae. Various multiplex PCR platforms, e.g., BD MAX™, Viper™, or Viper™ LT platforms, can be used to perform one or more steps of the disclosed methods. The methods can be performed in a multiplex fashion. For example, the nucleic acid amplification, in some embodiments, comprises performing multiplex PCR.

Samples

The methods and compositions disclosed herein can be used to detect the presence/absence and amount of *N. gonorrhoeae* in a wide variety of samples. As used herein, a "sample" refers to a sample taken from one or more number of subjects or sources that are suspected of containing or potentially contains *N. gonorrhoeae* nucleic acid.

The source from which the sample is collected is not limited. For example, the sample can be taken from a biological source, such as, tissue, blood, saliva, sputa, mucus, sweat, urine, urethra, urethral swabs, cervix, cervical swabs, penis, anus, throat, vagina, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The biological sample can be used (i) directly as obtained from the subject or source, or (ii) following a pre-treatment to modify the character of the sample. Thus, the test sample can be pre-treated prior to use, for example, by preparing plasma or serum from blood, disrupting cells or viral particles, preparing liquids from solid materials, diluting viscous fluids, filtering liquids, concentrating liquids, inactivating interfering components, adding reagents, purifying nucleic acids, and the like. Sample preparation can also include using a solution that contains buffers, salts, detergents, and/or the like which are used to prepare the sample for analysis. In some embodiments, the sample is processed before molecular testing. In some embodiments, the sample is analyzed directly, and is not pre-processed prior to testing.

The sample can be a biological sample, for example a clinical sample. In some embodiments, the sample can be collected from the urethra, penis, anus, throat, cervix, or vagina of a subject. In some embodiments, the biological sample is a vaginal sample.

Vaginal or urine samples are often infected with multiple organisms. The disclosed primers and probes are tolerant to mixed infections of the vaginal or urine matrix.

EXAMPLES

The following examples are provided to demonstrate particular situations and settings in which this technology may be applied and are not intended to restrict the scope of the invention and the claims included in this disclosure.

Example 1

Detection of Seventy-Two *N. gonorrhoeae* Clinical Isolates

Sample buffers were spiked with 72 *N. gonorrhoeae* clinical isolates/strains and heat lysed, respectively. BD MAX™ system was used to extract DNA from each sample solution, and the extracted DNA was amplified using opcA-6 PCR system shown in Table 1 to detect the presence of opcA gene region sequence in *N. gonorrhoeae*. As shown in FIGS. 2A-B, the opcA-6 system successfully identified all 72 different *N. gonorrhoeae* clinical isolates tested.

This example shows that the opcA-6 PCR system can be used to detect a wide variety of *N. gonorrhoeae* clinical isolates.

Example 2

Specificity Testing of opcA-6 PCR System

Sample buffers were spiked with *Neisseria* organisms and heat lysed, respectively. BD MAX™ system was used to extract DNA from each sample solution, and the extracted DNA was amplified using opcA-6 PCR system shown in Table 1 or Pilin qPCR system to detect the presence of *Neisseria* organisms in the sample solutions. As shown in FIG. 3A, the opcA-6 system resulted in no amplification product in any samples spiked with only non-gonorrhoeae *Neisseria*, and thus led no false positives for all the non-gonorrhoeae *Neisseria* species tested. As shown in FIG. 3B, the Pilin-based qPCR system cross-reacted with several non-gonorrhoeae *Neisseria* species (e.g., *N. cineria, N. sicca, N. lactamica*), while the opcA-6 system only generated amplification product in the sample spiked with *N. gonorrhoeae*.

This example shows that the opcA-6 PCR system is highly specific for *N. gonorrhoeae*, and does not cross-react with any non-gonorrhoeae *Neisseria* sequences.

Example 3

Specificity Testing of opcA-6 PCR System

Figures 4, 4A:
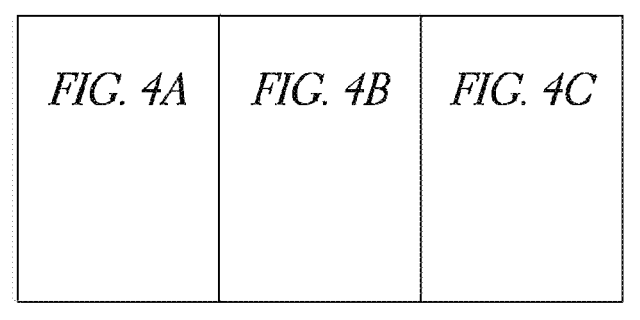

A sample buffer was spiked with organisms commonly found in a vaginal clinical sample and heat lysed, respectively. BD MAX™ system was used to extract DNA from the sample solution, and the extracted DNA was amplified using opcA-6 PCR system shown in Table 1. As shown in FIGS. 4A-C, the opcA-6 system did not cross-react with any of 115 organism spiked in the sample, and resulted in no amplification product.

This example shows that the opcA-6 PCR system is highly specific for *N. gonorrhoeae*, and does not cross-react with sequences of organisms commonly found in vaginal clinical samples.

Example 4

Detection Limits of opcA-6 PCR System

Figure 5:
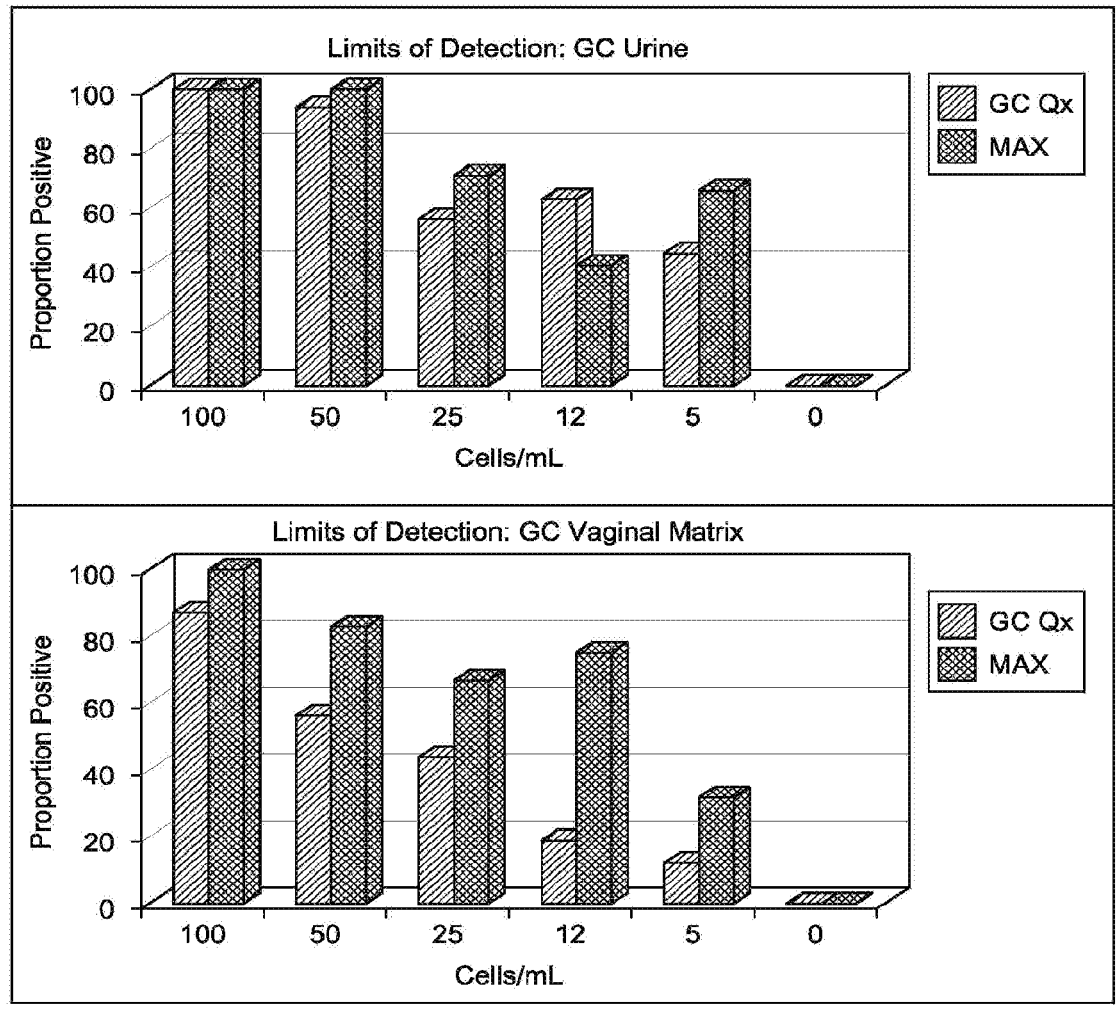
FIG. 5 shows histograms illustrating detection limits of the opcA-6 PCR system in detecting *N. gonorrhoeae* in clinical urine and vaginal matrix samples using BD MAX and Viper XT extraction methods.

Clinical urine and vaginal matrix samples were spiked with *N. gonorrhoeae* and heat lysed. BD MAX™ and Viper™ XTR system were used to extract DNA from the samples, respectively, and the extracted DNA was amplified using opcA-6 PCR system shown in Table 1 to determine the detection limits of the system. The results are shown in FIG. 5. As shown in FIG. 5, the opcA-6 qPCR system had a greater proportion positive on the MAX™ system than the *N. gonorrhoeae* amplification system currently used on the Viper™ XTR system (labeled as GC Qx in FIG. 5).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A composition for use in the detection of the presence of a major outer protein gene (opcA) sequence from *Neisseria gonorrhoeae* in a biological sample comprising at least one pair of primers comprising a first primer consisting of SEQ ID NO: 1 and a second primer consisting of SEQ ID NO: 2, wherein each primer comprises at least one non-conventional substitution of a base, a sugar or a backbone linkage, and a oligonucleotide probe comprising an oligonucleotide consisting of SEQ ID NO: 3 and a detectable fluorescent moiety.

* * * * *